(12) United States Patent
Pohl et al.

(10) Patent No.: US 8,361,745 B2
(45) Date of Patent: Jan. 29, 2013

(54) HUMAN GROWTH AND DIFFERENTIATION FACTOR GDF-5

(75) Inventors: Jens Pohl, Hambruecken (DE); Frank Ploeger, Heidelberg (DE)

(73) Assignee: Biopharm Gesellschaft zur Biotechnologischen Entwicklung von Pharmaka mbH, Heidelberg (DE)

( * ) Notice: Subject to any disclaimer, the term of this patent is extended or adjusted under 35 U.S.C. 154(b) by 140 days.

(21) Appl. No.: 12/374,080

(22) PCT Filed: Jul. 17, 2007

(86) PCT No.: PCT/EP2007/006331
§ 371 (c)(1),
(2), (4) Date: Jan. 16, 2009

(87) PCT Pub. No.: WO2008/009419
PCT Pub. Date: Jan. 24, 2008

(65) Prior Publication Data
US 2010/0129342 A1 May 27, 2010

(30) Foreign Application Priority Data
Jul. 18, 2006 (EP) .................................. 06014928

(51) Int. Cl.
| | |
|---|---|
| C12N 15/00 | (2006.01) |
| C12N 15/09 | (2006.01) |
| C12N 15/12 | (2006.01) |
| C12N 15/19 | (2006.01) |
| A61K 38/00 | (2006.01) |
| A61K 38/16 | (2006.01) |
| A61K 38/17 | (2006.01) |
| A61K 38/18 | (2006.01) |
| A61K 38/19 | (2006.01) |

(52) U.S. Cl. ................... 435/69.1; 435/320.1; 435/69.4; 435/69.5; 435/71.2; 514/7.6; 514/8.8; 514/8.9; 514/9.4; 536/23.1; 536/23.5

(58) Field of Classification Search ........................ None
See application file for complete search history.

(56) References Cited

U.S. PATENT DOCUMENTS

| | | | | |
|---|---|---|---|---|
| 5,801,014 A | * | 9/1998 | Lee et al. ..................... | 435/69.1 |
| 5,935,815 A | * | 8/1999 | van de Ven et al. .......... | 435/69.1 |
| 6,344,541 B1 | * | 2/2002 | Bass et al. .................... | 530/324 |
| 2002/0045568 A1 | * | 4/2002 | Hotten et al. .................... | 514/2 |
| 2005/0054570 A1 | * | 3/2005 | Rosen et al. ..................... | 514/12 |

FOREIGN PATENT DOCUMENTS

| | | |
|---|---|---|
| WO | 97/03188 A | 1/1997 |
| WO | 2005093071 A1 | 10/2005 |

OTHER PUBLICATIONS

Sieber et al. (Apr. 2006, Biol. Chem. 387:451-460).*
Hammonds, Jr. et al., 1991, Molecular Endocrinology 5:149-155.*
Hoetten et al., "Cloning and expression of recombinant human growth/differentiation factor 5", Biochemical and Biophysical Research Communications, vol. 204, No. 2, Oct. 28, 1994, pp. 646-652.
Schreuder et al., "Crystal structure of recombinant human growth and differentiation factor 5: Evidence for interaction of the type I and type II receptor-binding sites", Biochemical and Biophysical Research Communications, vol. 329, No. 3, Apr. 15, 2005, pp. 1076-1086.
Schmidt, "Recombinant expression systems in the pharmaceutical industry", Applied Microbiology and Biotechnology, vol. 65, No. 4, Sep. 2004, pp. 363-372.
Ashraf et al., "A novel multi-affinity tag system to produce high levels of soluble and biotinylated proteins in *Escherichia coli*", Protein Expression & Purification, (2004), vol. 33, pp. 238-245.
Jin et al., "Refolding and purification of unprocessed porcine myostatin expressed in *Escherichia coli*", Protein Expression & Purification, (2004), vol. 35, pp. 2-11.

* cited by examiner

*Primary Examiner* — Elizabeth C Kemmerer
(74) *Attorney, Agent, or Firm* — Rothwell, Figg, Ernst & Manbeck, P.C.

(57) ABSTRACT

This invention relates to the production and use of pharmaceutical growth factor compositions with novel characteristics, e.g., improved solubility and controlled release characteristics under physiological conditions. Compositions of one or more precursor proteins of growth factors of the GDF family provoke morphogenic effects, such as growth, differentiation, protection and regeneration of a variety of tissues and organs, e.g., bone, cartilage, tendons, ligaments, nerves and skin. These compositions can be advantageously used for the healing of tissue-destructive injuries and for the prevention or therapy of degenerative disorders.

23 Claims, 10 Drawing Sheets

```
  1 MRLPKLLTFL LWYLAWLDLE FICTVLGAPD LGQRPQGTRP GLAKAEAKER PPLARNVFRP
 61 GGHSYGGGAT NANARAKGGT GQTGGLTQPK KDEPKKLPPR PGGPEPKPGH PPQTRQATAR
121 TVTPKGQLPG GKAPPKAGSV PSSFLLKKAR EPGPPREPKE PFRPPPITPH EYMLSLYRTL
181 SDADRKGGNS SVKLEAGLAN TITSFIDKGQ DDRGPVVRKQ RYVFDISALE KDGLLGAELR
241 ILRKKPSDTA KPAAPGGGRA AQLKLSSCPS GRQPASLLDV RSVPGLDGSG WEVFDIWKLF
301 RNFKNSAQLC LELEAWERGR AVDLRGLGFD RAARQVHEKA LFLVFGRTKK RDLFFNEIKA
361 RSGQDDKTVY EYLFSQRRKR RAPLATRQGK RPSKNLKARC SRKALHVNFK DMGWDDWIIA
421 PLEYEAFHCE GLCEFPLRSH LEPTNHAVIQ TLMNSMDPES TPPTCCVPTR LSPISILFID
481 SANNVVYKQY EDMVVESCGC R
```

FIG. 1

```
hGDF-6 : CSKRPLHVNFKELGWDDWIIAPLEYEAYHCEGVCDFPIRSHLEPTNHAIIQTLMNSMDPGSTPPSCCVPTKLTPISILYIDAGHNVV : 87
hGDF-7 : CSRKPLHVDFKELGWDDWIIAPLDYEAYHCEGLCDFPIRSHLEPTNHAIIQTLLNSMAPDAAPASCCVPARLSPISILYIDAANNVV : 87
hGDF-5 : CSRKALHVNFKDMGWDDWIIAPLEYEAFHCEGLCPFPIRSHLEPTNHAVIQTLMNSMDPESTBPTCCVPTRLSPISILFIDSANNVV : 87 hGDF-6 : YKQYEDMVVESCGCR
hGDF-7 : YKQYEDMVVEACGCR
hGDF-5 : YKQYEDMVVESCGCR
```

FIG. 2

% sequence identity to cystine-knot-domain of human GDF-5

| Sequence | % Identity | Identical Residues |
|---|---|---|
| GDF-5 Homo | 100 | 102/102 |
| GDF-5 Mus | 99 | 101/102 |
| GDF-6 Mus | 86 | 88/102 |
| GDF-6 Homo | 85 | 87/102 |
| GDF-6 Xenopus | 84 | 86/102 |
| GDF-6 Bos | 83 | 85/102 |
| GDF-7 Homo | 81 | 83/102 |
| GDF-7 Macaca | 80 | 82/102 |
| GDF-7 Mus | 80 | 82/102 |
| BMP-4 | 57 | 58/102 |
| Vg-1 | 52 | 53/102 |
| DPP | 52 | 53/102 |
| BMP-5 | 52 | 53/102 |
| BMP-9 | 51 | 52/102 |
| BMP-10 | 51 | 52/102 |
| BMP-8A | 51 | 51/102 |
| BMP-6 | 51 | 52/102 |
| BMP-7 | 51 | 52/102 |
| GDF-3 | 49 | 50/102 |
| 60A | 48 | 49/102 |
| BMP-8B | 48 | 49/102 |
| BMP-3A | 47 | 48/103 |
| GDF-9B | 45 | 46/102 |
| BMP-3B | 43 | 44/103 |
| GDF-8 | 37 | 38/102 |
| GDF-12 | 37 | 38/104 |
| GDF-11 | 36 | 37/102 |
| GDF-9 | 32 | 33/102 |

FIG. 3

MGSSHHHHHHSSGLVPRGSHMAPDLGQRPQGTRPGLAKAEAKERPPLARNVFR
PGGHSYGGGATNANARAKGGTGQTGGLTQPKKDEPKKLPPRPGGPEPKPGHPP
QTRQATARTVTPKGQLPGGKAPPKAGSVPSSFLLKKAREPGPPREPKEPFRPP
PITPHEYMLSLYRTLSDADRKGGNSSVKLEAGLANTITSFIDKGQDDRGPVVR
KQRYVFDISALEKDGLLGAELRILRKKPSDTAKPAAPGGGRAAQLKLSSCPSG
RQPASLLDVRSVPGLDGSGWEVFDIWKLFRNFKNSAQLCLELEAWERGRAVDL
RGLGFDRAARQVHEKALFLVFGRTKKRDLFFNEIKARSGQDDKTVYEYLFSQR
RKRRAPLATRQGKRPSKNLKARCSRKALHVNFKDMGWDDWIIAPLEYEAFHCE
GLCEFPLRSHLEPTNHAVIQTLMNSMDPESTPPTCCVPTRLSPISILFIDSAN
NVVYKQYEDMVVESCGCR

FIG. 4

HUMAN GROWTH AND DIFFERENTIATION FACTOR GDF-5

CROSS REFERENCE TO RELATED APPLICATION

This application is a 35 U.S.C. 371 National Phase Entry Application from PCT/EP2007/006331, filed Jul. 17, 2007, which claims the benefit of European Patent Application No. 06 014 928.3, the disclosure of which is incorporated herein in its entirety by reference.

This invention relates to the production and use of pharmaceutical growth factor compositions with novel characteristics, e.g. improved solubility and controlled release characteristics under physiological conditions. Said compositions of one or more precursor proteins of growth factors of the GDF family provoke morphogenic effects such as for example growth, differentiation, protection and regeneration of a variety of tissues and organs, e.g. bone, cartilage, tendons, ligaments, nerves and skin. The invention can be advantageously used for the healing of tissue-destructive injuries and for the prevention or therapy of degenerative disorders.

A growth factor with a variety of biological attributes is growth/differentiation factor 5 (GDF-5). The protein is also known as MP52, very close relatives of GDF-5 with overlapping biological functions and extremely high amino acid homologies are GDF-6 and GDF-7. The GDF-5/-6/-7 group is conserved among vertebrate/mammalian species but does not have known orthologues in invertebrates (Ducy and Karsenty 2000, Kidney Int. 57, 2207-2214). In general, GDF proteins promote cell proliferation and differentiation as well as tissue formation/regeneration and are relevant for a wide range of medical treatment methods and applications. These dimeric molecules act through specific receptor complexes that are composed of type I and type II serine/threonine receptor kinases. The receptor kinases subsequently activate smad proteins, which then propagate the signals into the nucleus to regulate target gene expression. Smad independent signalling pathways are also initiated by these receptors and result in induction of the MAP Kinase pathway. Smads are a unique family of signal transduction molecules that can transmit signals directly from the cell surface receptors to the nucleus, where they regulate transcription by interacting with DNA binding partners as well as transcriptional coactivators and corepressors.

The members of this protein family are initially synthesized as large precursor proteins which subsequently undergo proteolytic cleavage at a cluster of basic residues approximately 110-140 amino acids from the C-terminus, thus releasing the C-terminal mature protein parts from the N-terminal prodomain. All mature polypeptides are structurally related and contain a conserved bioactive domain comprising six or seven canonical cysteine residues which are responsible for the three-dimensional "cystine-knot" motif of these proteins.

Within the mammalian body, endoproteolytic cleavage takes primarily place in the trans-Golgi network. The process finally leads to the secretion of active mature protein parts, whereas the source material as well as the prodomain portion of the cleaved precursor protein is believed to remain in the Golgi compartment.

Pharmaceutical compositions comprising biologically active mature GDF-5 related proteins have already been developed (see e.g. WO96/33215). Mature GDF-5 has been identified to be a very effective promoter of bone, cartilage and connective tissue formation (see for example WO 95/04819, Hötten et al. 1996, Growth Factors 13, 65-74; Storm et al. 1994, Nature 368, 639-643; Chang et al. 1994, J. Biol. Chem. 269, 28227-28234). It is also beneficial for promoting regeneration of various tissues and organs. GDF-5 is a growth factor in the nervous system and supports the survival of e.g. dopaminergic neurons (see for example WO 97/03188; Krieglstein et al., (1995) J. Neurosci Res. 42, 724-732; Sullivan et al., (1997) Neurosci Lett 233, 73-76; Sullivan et al. (1998), Eur. J. Neurosci 10, 3681-3688). The protein allows to maintain nervous function or to retain nervous function in already damaged tissues. GDF-5 is therefore considered to be a generally applicable neurotrophic factor. It is also useful for the treatment and diagnosis of skin related disorders (WO 02/076494; Battaglia et al. 2002, Trans. Orthop. Res. Soc. 27, 584), and for induction of angiogenesis (Yamashita et al. 1997, Exp. Cell Res. 235, 218-26).

Especially the osteogenic properties of GDF-5 have been successfully used in the past, i.e. to aid the healing of local bone fractures. For such purposes, combined osteoinductive materials consisting of mature GDF-5 and solid carrier matrices have been developed (see for example WO98/21972). However, solid materials are inappropriate for indications such as i.e. osteoporosis which require a systemic application in order to guarantee a homogeneous distribution of the protein within the body. Likewise problematic is a drug delivery to places which are badly accessible such as the brain or the spinal cord.

In these cases, administration of GDF-5 in soluble form is generally preferred. However, the mature protein shows exceptional poor solubility under physiological conditions. According to this fact, previous attempts to formulate stable liquid or gel-like GDF-5 compositions have faced serious problems. A pH-dependent solubility profile of mature GDF-5/MP52 (shown i.e. in EP 1 462 126) reveals that the protein starts precipitating in aqueous solutions with a pH above 4.25 and becomes almost insoluble between pH 5 and pH 9. Although EP 1 462 126 succeeded in improving the protein solubility profile slightly by using solvents with low ionic strength, high solubility at nearly neutral pH has never been achieved but is very desirable for parenteral and other formulations.

After discovery of their unique tissue inductive activities, growth factor proteins such as GDF-5 have been successfully applied in therapeutic research and regenerative surgery, in which they promote and assist the natural healing process of damaged tissues, either alone or in combination with specific matrix materials. Nevertheless there is still a great need to develop novel methods and pharmaceutical compositions for the efficient administration of such proteins under physiological conditions, e.g. in cases which do not allow the combination of the protein with a voluminous solid carrier material. Especially desirable are formulations from which the active protein is released in a controlled manner which exactly satisfies the demand of the body.

It is therefore an object of the invention to improve and facilitate the medical use of GDF-5 and related proteins by providing liquid growth factor compositions which are stable, non-toxic and applicable at physiological pH values. This object comprises the development of injectable and/or parenteral formulations, controlled release compositions, and formulations which can be transported across the blood-brain barrier. A second object of the invention is a method for the preparation of said formulations and compositions. A third object of the invention is to provide suitable methods for the local or systemic administration of said growth factor compositions.

These objects are solved according to the invention by providing pharmaceutical compositions containing biologically inactive precursor proteins related to human Growth/Differentiation Factor 5 (hGDF-5). These pharmaceutical compositions are intended to serve as controlled release formulations which are delayed activated inside the mammalian body, either by endogenous proteases at the target site or by co-administered proteolytic enzymes.

Some frequently used terms herein are defined and exemplified as follows:

The term "cystine-knot-domain" as used herein means the well known and conserved cysteine-rich amino acid region which is present in growth/differentiation factors (GDFs) and which forms a three-dimensional protein structure known as cystine-knot. In this domain, the respective location of the cysteine residues to each other is important and is only allowed to vary slightly in order not to lose the biological activity. Consensus sequences for cystine-knot domains are known in the state of the art. According to the definition defined herein the cystine-knot-domain of a protein starts with the first cysteine residue participating in the cystine-knot of the respective protein and ends with the residue which follows the last cysteine participating in the cystine-knot of the respective protein. For example, the cystine-knot domain of the human GDF-5 full length (precursor) protein (SEQ ID NO 1) comprises the amino acids 400-501 (see also FIG. 1).

The term "precursor protein" as used herein means a biologically inactive protein comprising a protease site, said site being necessary for proteolytic cleavage of said precursor protein and subsequently leading to the release of a biologically active mature protein.

The term "GDF-5 related precursor protein(s)" as used herein means any naturally occurring mammalian or artificially created, biologically inactive precursor protein which comprises a) a protease site which is necessary for proteolytic cleavage of said precursor protein, subsequently leading to the release of a biologically active mature protein, and b) a cystine-knot-domain with an amino acid identity of at least 70% to the 102 aa cystine-knot domain of human GDF-5 (amino acids 400-501 of FIG. 1/SEQ ID NO 1).

The percentage of identical residues can be easily determined by alignment of two sequences as described hereinafter, followed by counting of the identical residues. This term includes proteins belonging to the group of GDF-5, GDF-6 and GDF-7 precursor proteins from each mammalian species as well as recombinant variants thereof as long as these proteins fulfil the above mentioned requirements. Non-limiting examples of GDF-5 related precursor protein are precursor proteins of human GDF-5 (disclosed as MP52 in WO95/04819 and in Hötten et al. 1994, Biochem. Biophys Res. Commun. 204, 646-652), recombinant human GDF-5/MP52 (WO96/33215), mouse GDF-5 (U.S. Pat. No. 5,801,014), CDMP-1 (WO96/14335), HMW human MP52s (WO97/04095), human GDF-6 (U.S. Pat. No. 5,658,882), mouse GDF-6 (NCBI accession no NP_038554), GDF-6/CDMP-2 (WO96/14335), human GDF-7 (U.S. Pat. No. 5,658,882), mouse GDF-7 (NCBI accession no AAP97721), GDF-7/CDMP-3 (WO96/143335), monomeric GDF-5, -6 and -7 (WO 01/11041 and WO99/61611).

The term "variant(s)" as used herein means any of the following polypeptides:
a) fragments of said protein comprising at least the cystine-knot domain and the protease site necessary for proteolytic activation.
b) protein constructs which contain additional sequences in excess to the original sequence of said protein
c) any combination of a) and b)

The term "biological activity" denotes the biological activities of a GDF-5 related protein or GDF-5 related precursor protein. For example, this activity can be measured by one or more of the following assays:

a) Osteogenic and chondrogenic activity can be measured by an in vitro alkaline phosphotase assay (ALP), e.g. as described in Takuwa et al. (1989), Am. J. Physiol. 257, E797-E803). This is the most useful and preferred in vitro test, which is demonstrated hereinafter in example 4. Mature growth factors have been shown to increase alkaline phosphatase activity i.e. in ROB-C26 osteoprogenitor cells (Yamaguchi et al. 1991, Calcif. Tissue Int. 49, 221-225) as described in WO95/04819, in embryonic ATDC5 cells (Riken Gene Bank, ROB 0565), in mouse stromal MCHT-1/26 cells, and in periodontal ligament (HPDL) cells as shown in Nakamura et al. 2003, J. Periodontal Res. 38,597-605.

b) Neurotrophic activity can be determined by increased survival of dopaminergic neurons as described for example by Krieglstein et al. 1995 (J. Neuroscience Res. 42, 724-732) or Sullivan et al. 1997 (Neuroscience Letters 233, 73-76);

c) the outgrowth of nerve fibers can be measured from embryonic retina as described i.e. in WO97/03188;

d) the angiogenic potential of these proteins can be determined for example in an in vivo corneal micropocket model as described in Yamashita et al. 1997 (Exp. Cell Research 235, 218-226);

e) effects of GDF-5-related proteins on the terminal differentiation of myoblasts is described e.g. by Inada et al 1996 (Biochem Biophys Res Commun. 222, 317-322);

f) in vivo tests measuring the inductive potential of such proteins concerning tendon and ligament e.g. are disclosed in Wolfman et al. 1997, J. Clin. Invest. 100, 321-330;

g) measurement of the signal transduction cascade through the activation of Smads using a reportergene assay based on the Smad-binding-elements preceding the firefly luciferase gene e.g. are previously described in Nohe et al., 2002. J Biol Chem. 277, 5330-5338.

Unlike their mature counterparts, precursor forms of GDF-5 related proteins are biologically inactive regarding their growth and differentiation capabilities. In addition, efficient production of these protein precursors in prokaryotic hosts failed seriously in the past due to unknown reasons, although in contrast production of the significantly shorter mature proteins is possible and has been achieved previously (see e.g. Hötten et al., Biochem Biophys Res Comm 204, 646-652 (1994). Because of these two facts, addition of GDF-5 related precursors to pharmaceutical compositions instead of mature proteins never seemed to be a reasonable option in the past.

According to the present invention, it has now surprisingly been found (and it is subsequently demonstrated hereinafter) that specific sequence modifications in fact allow for the recombinant expression of GDF-5 related precursor proteins in prokaryotic hosts, a process which is economically desirable.

It is furthermore shown that these recombinant proteins, although expressed in bacteria and therefore lacking essential eukaryotic features such as e.g. glycosylation, can be proteolytically cleaved and activated by selected proteases in a manner comparable to glycosylated eukaryotic precursor proteins. It is also demonstrated that these recombinant precursor forms, unlike their mature counterparts, are soluble at physiological pH values and can be used to formulate pharmaceutical compositions for the therapy of tissue destructive disorders. It is finally substantiated that the disclosed pharmaceutical compositions comprising said precursor molecules might be beneficially utilized as initially inactive controlled release formulations. These formulations can be parenterally administered and are subsequently activated in situ.

It is therefore a first object of the present invention to provide suitable methods for the heterologous recombinant expression of GDF-5 related precursor proteins in prokaryotic host cells such as e.g. E. coli. Such prokaryotic production is cost effective, efficient and of considerable commercial interest. Although it is known that mature GDF-5 related proteins are recombinantly producible in bacteria without major problems, similar attempts to manufacture precursor molecules of these proteins in sufficient quantities in E. coli failed in the past. It has been postulated previously that the prodomain of the precursor protein may comprise partial sequences which are deleterious or even toxic for bacteria. However, according to the present invention, this explanation is no longer acceptable because it is shown hereinafter that prokaryotic expression of the complete precursor sequence is achievable if certain amino acids are added to the original amino acid sequence. More precisely, an amino-terminal sequence extension of at least five, preferably six or seven amino acids, is sufficient to allow bacterial production of the protein. The following table shows a selection of tested plasmid/bacterial strain combinations for the expression of GDF-5 related precursor proteins. Note that only constructs comprising a DNA coding for an aminoterminal basic elongation of the precursor protein led to the expression of precursor proteins.

| Plasmid (SP = Signal Peptide) | Bacterial Strain | Expression +: good, +++: high |
|---|---|---|
| pKOT (Tac-Promotor), +SP | W3110 BP | no |
| pKOT (Tac-Promotor), +SP | BL21 (DE3) | no |
| pKOT (Tac-Promotor), −SP | W3110 BP | no (37° C.) |
| pKOT (Tac-Promotor), −SP | W3110 BP | no (22° C.) |
| pKOT (Tac-Promotor), −SP | BL21 (DE3) Lys | no |
| pKOT (Tac-Promotor), −SP | Origami (DE3) | no |
| pKOT (Tac-Promotor), −SP | HMS174 (DE3) | no |
| pGEM (T7-Promotor), −SP | BL21 (DE3) | no |
| pGEM (T7-Promotor), −SP | JM109 | No |
| pET15b (T7-Promotor), Basic-tag | BL21 (DE3) | Yes (+) |
| pET15b (T7-Promotor), Basic-tag (Optimized Codon Usage) | Rosetta | Yes (+++) |
| pKOT (Tac-Promotor), −SP | Rosetta | no |
| pKOT (Tac-Promotor), +SP | Rosetta | No |

The results disclosed herein demonstrate that said sequence extension is especially beneficial if it comprises a continuous stretch of five or more basic amino acids (arginine, histidine or lysine) which forces the bacterial cell to produce the protein.

In a preferred embodiment of this part of the invention, the N-terminus of such fusion protein comprises the sequence HHHHH (5×histidine, SEQ ID NO: 7). Especially preferred are precursor proteins which comprise a continuous stretch of 6 histidines. For reasons of precaution it is noted that said basic stretch is only needed for the protein production within the bacterial cell and is not required for already established industrial protein purification techniques.

In other preferred embodiments, the N-terminus comprises the sequences LLLLL (SEQ ID NO: 8), RRRRR (SEQ ID NO: 9), HLHLH (SEQ ID NO: 10) or RHRHR (SEQ ID NO: 11).

If a fusion protein is generally unwanted, it is of course also possible to modify the original protein sequence without addition of amino acids, i.e. by simply replacing a part of the original protein sequence by said continuous stretch of five or more basic amino acids. However, it is required that such replacement should be done within the first 10 amino acids of the original protein sequence.

Non-parenteral administration of a protein comprising an amino-terminal extension or a modification comprising a basic stretch of amino acids into mammals might create some immunogenic problems. To avoid an undesired immune response, it is helpful if the modified or added amino acid sequence of the bacterially expressed GDF-5 related precursor protein can be removed prior to the administration to mammalian patients. Removal can be easily achieved by different techniques, e.g. if an adequate protease site (which is different from the protease site required for biological activation) is recombinantly introduced into the protein sequence of the GDF-5 related precursor protein. In a preferred embodiment, said protease site is selected from the group consisting of sites for thrombin, enterokinase, factor Xa or sumo protease.

As an alternative, the N-terminal extension of the GDF-5 precursor protein might also be removed by an autocatalytic cleavage process induced either by pH-shift or reducing agents such as DTT or beta mercaptoethanol (see example 7). For example, the inducible self-cleavage activity of protein splicing elements such as e.g. inteins can be used to separate the GDF-5 precursor protein from the N-terminal affinity tag.

For this purpose, the GDF-5 precursor protein can e.g. be integrated in vectors such as the commercially available IMPACT-TWIN (Intein Mediated Purification with Affinity Chitin-binding Tag-Two Intein, New England Biolabs) system. IMPACT-TWIN is able to isolate native recombinant proteins without the use of exogenous proteases. Intein1 is a mini-intein derived from Synechocystis spdnaB gene and engineered to undergo pH and temperature dependent cleavage at its C-terminus (Mathys et al. (1999), Gene 231, 1-13). Intein2 is either a mini-intein from the *Mycobacterium xenopi* gyrA gene (pTWIN1) or from the *Methanobacterium thermoautotrophicum* rir1 gene (pTWIN2). These inteins have been modified to undergo thiol-induced cleavage at their N-terminus (Southworth et al., (1999) Biotechniques 27, 110-120). The use of thiol reagents such as 2-mercaptoethanesulfonic acid (MESNA) releases a reactive thioester at the C-terminus of the target protein.

It has additionally been found that the recombinant expression of said GDF-5 related precursor protein in prokaryotes can be also enhanced by other genetic modifications. This enhancement requires that certain DNA triplets encoding the amino acids isoleucine, arginine, leucine, proline and glycine, which appear to be detrimental for the expression of the recombinant precursor proteins in bacteria, have to be removed from a part of the DNA coding for the GDF-5 related precursor protein.

More precisely, in another preferred embodiment of this part of the invention, bacterial expression of a GDF-5 related precursor protein is clearly facilitated if triplets AUA (Ile), AGG, AGA, CGG, CGA (Arg), CUA (Leu), CCC (Pro) and GGA (Gly) have been replaced by alternative triplets of the genetic code encoding identical amino acids. As shown in FIG. 5, such optimized codon usage has been implemented in a pET15b (T7-Promotor, Basic-tag) vector system. Expression of the precursor protein in the E. coli strain Rosetta with optimized codon usage resulted in a high yield protein production. Use of a similar vector system but without optimized codon usage in bacterial strain BL21(DE3) yielded lower amounts of the precursor protein.

In the most preferred embodiment of this part of the invention, a continuous stretch of two or more of said detrimental triplets within the first 30 codons of said DNA molecule has to be avoided.

The yield and quality of the GDF-5 related precursor protein can be further dramatically improved if the bacterial production method comprises optimized purification steps. It has been found out that best results are achieved if the purification process comprises a direct refolding step. Direct refolding means that the expressed proteins are used directly after inclusion body preparation in a refolding procedure (necessary for renaturation) without prior column purification step. Usually GDF-5 related proteins are column purified before initiation of refolding, see e.g. WO96/33215). Especially important for the disclosed direct refolding procedure is the use of an optimized buffer for solubilization of inclusion bodies containing not more than 3 mM DTT. It has been found out that more DTT content interferes with the refolding procedure, which highly depends on a redox system which is sensitive to reducing agents like DTT. Due to the low amount of DTT, the refolding step can be performed in a 1:10 dilution instead of a commonly used 1:100 dilution, thus having positive effects on the protein yield. Specific parameters of these preferred purification conditions are disclosed in example 1.

GDF-5 related precursor proteins which are manufactured in bacteria by the aforementioned methods have a variety of advantages besides their cost effective production. It is also essential that the recombinant precursor proteins of the invention, although expressed in bacteria and therefore lacking essential eukaryotic features such as e.g. glycosylation, can be proteolytically cleaved and activated in a manner comparable to precursor proteins expressed in eukaryotes. Proteolytic cleavage of proteins belonging to the family of growth and differentiation factors often occurs at a characteristic RX(K/R)R (SEQ ID NO: 12) site that divides the mature peptide from the aminoterminal prodomain. For example, the cleavage site of human GDF-5 contains the motif RRKRSEQ ID NO: 13), whereas the corresponding sites of GDF-6 and GDF-7 contain the sequence RRRR (SEQ ID NO: 14). These sites are known to be recognized by subtilisin like proprotein convertases (SPCs), a family of seven structurally related serine endoproteases (designated SPC1 to SPC7). Although all subtilisin-like proprotein convertases can be used for the cleavage of the precursor proteins of the invention, protease SPC1 (also designated furin) is especially useful. Also preferred are SPC4, SPC6 and SPC7 because they are coexpressed with growth factor proteins at distinct sites (see Costam et al. 1996, J. Cell Biol. 134, 181-191). Especially preferred according to the invention is furthermore the addition of single SPCs or combinations of different SPCs in pharmaceutical compositions comprising GDF-5 related precursor proteins. Suitable combinations are e.g. SPC1 and SPC4, SPC1 and SPC6, and SPC1 and SPC7. Another preferred option is the cleavage of the precursor proteins with trypsin (as shown in FIG. 7).

The extracellullar matrix is believed to serve as storage site for growth and differentiation factors. Thus, also suitable to release active mature protein from the precursor proteins of the invention are other matrix proteases, e.g. matrix metalloproteases, preferably MMP3.

As a non-limiting example, FIG. 6 and example 3 show the cleavage of a bacterially produced precursor protein of the invention (human GDF-5 precursor) with proprotein convertase SPC1 (also designated furin). In mammals, furin is predominantly localized within the trans-Golgi network (TGN)/endosomal system, but has also been detected on the cell surface and extracellularly (Molloy et al., 1999).

FIG. 7 and example 4 (ALP activity assay) demonstrate that the mature GDF-5 protein, which is released from the cleaved recombinant precursor by selected proteases furin, trypsin and MMP3, exhibits significant biological activity, whereas the recombinant precursor protein itself is biologically inactive.

The GDF-5-related precursor proteins as defined herein comprise a) a protease site necessary for proteolytic activation and b) a cysteine-knot-domain with an amino acid identity of at least 70% to the 102 aa cysteine-knot domain of human GDF-5. Preferred are precursor proteins comprising a cysteine-knot domain with an amino acid identity of at least 75%, preferably at least 80%, more preferably at least 85%, more preferably at least 90%, more preferably at least 95% to the 102 aa cysteine-knot domain of human GDF-5. However, the limiting value of at least 70% is well suitable to separate members of the GDF-5/-6/-7 group of proteins as well as variants thereof from precursors of other proteins such as other GDFs and other growth factors. A comparison of the 102 aa cysteine-knot-domains of human GDF-5, human GDF-6 and human GDF-7 (FIG. 2) reveals the high grade of amino acid identity between these proteins. Human GDF-6 shares 87 (85%) and human GDF-7 83 (81%) identical residues with the cysteine-knot-domain of human GDF-5. In contrast, GDFs and BMPs not belonging to the GDF-5/-6/-7 subgroup display much lower identity values below 60%.

The determination of corresponding amino acid positions in related amino acid sequences as well as the calculation of percentages of identity between can be performed with the help of well known alignment algorithms and optionally computer programs using these algorithms. The amino acid identities in this patent application have been calculated by aligning sequences with the freeware program ClustalX (Version 1.81) with default parameters and subsequent counting of identical residues by hand. Default settings for pairwise alignment (slow-accurate) are: gap opening parameter: 10.00; gap extension parameter 0.10; Protein weight matrix: Gonnet 250. The ClustalX program is described in detail in:

Thompson, J. D., Gibson, T. J., Plewniak, F., Jeanmougin, F. and Higgins, D. G. (1997)

The ClustalX windows interface: flexible strategies for multiple sequence alignment aided by quality analysis tools.

Nucleic Acids Research 24:4876-4882.

ClustaiX is a windows interface for the ClustalW multiple sequence alignment program and is i.e. available from various sources, i.e. by anonymous ftp from ftp-igbmc.u-strasbg.fr, ftp.embl-heidelberg.de, ftp.ebi.ac.uk or via download from the following webpage: www-iqbmc.u-strasbq.fr/Biolnfo/. The ClustalW program and algorithm is also described in detail in:

Thompson, J. D., Higgins, D. G. and Gibson, T. J. (1994)

CLUSTALW: improving the sensitivity of progressive multiple sequence alignment through sequence weighting, positions-specific gap penalties and weight matrix choice. Nucleic Acids Research 22:4673-4680.

As already explained and shown in example 6 (FIG. 9, respectively), the recombinant precursor proteins of the invention are biologically inactive but can be activated in vivo/in situ by proteases. This is especially advantageous in cases where precursor proteins or pharmaceutical compositions comprising said precursor proteins are therapeutically administered to a patient. Since proteases like e.g. SPCs are detectable in the Golgi network but are also located in other cell compartments and the extracellular matrix in various amounts in dependency of the bodies need, they are able to convert administered protein precursors to active mature proteins by and by in a manner controlled by the mammalian metabolism. Thus, administration of protein precursors guarantees a sustained release of the active drug over a longer period and avoids dosage problems as known from the administration of mature/active growth factors.

Although the administration of pure GDF-5 related precursor proteins should be sufficient for some therapeutic purposes, other indications may require the administration in combination with protease formulations comprising e.g. Trypsin, SPCs and matrix metalloproteases, for example because some tissues are characterized by the lack of endogenous protease production.

It should also be mentioned that SPCs and other proteases show distinct tissue specific expression patterns. It is well known that some are ubiquitously present whereas others are restricted to a certain tissue. Although the precursor proteins of the invention can be activated e.g. by SPC1/furin alone (see example 3), the tissue specific expression should be taken into account if pharmaceutical compositions comprising precursor proteins in combination with proteases are administered. In some cases, precursor protein activation in some tissues may be enhanced if the pharmaceutical compositions comprise a protease with strong expression pattern in said tissue. In other cases, two or more proteases are beneficial for full activation. For example, it is known that SPC2, SPC3 and SPC4 expression is largely confined to neuronal tissues, whereas GDF-5 is activated in joints by a combination of two SPCs, namely SPC1 (Furin) and SPC6. SPC4 and SPC6 expression in developing limbs overlaps with that of Growth and differentiation factors. SPC7 seems to be ubiquitously expressed.

Additional expression patterns of SPCs are well known from various publications, see e.g. Seidah et al. 1990, DNA Cell Biol. 9, 415-424; Nakayama et al. 1992, J. Biol. Chem. 257, 5897-5900; Beaubien et al. 1995, Cell Tiss. Res. 279, 539-549; Dong et al. 1995, J. Neurosci. 15, 1778-1796). If desired, such expression patterns can also be easily determined by routine techniques such as in situ hybridization, antibody staining, or RT-PCR.

In an especially preferred embodiment of this part of the invention, a pharmaceutical composition comprising a precursor protein and a protease formulation is designed in a way which provides retarded release of said proteases. This composition ensures that the precursor proteins of the invention are activated at a time point when the administered solution reaches the target site. There are countless methods for the sustained release of proteins described in the art which can be used. For a review see e.g. Handbook of Pharmaceutical Controlled Release Technology (Wise, D., ed.), 2000. For example, a slow-release formulation may comprise proteins bound to or incorporated into particulate preparations of polymeric compounds (such as polylactic acid, polyglycolic acid, etc.) or liposomes.

In another embodiment of this part of the invention, the protease formulation is administered separately a certain time period after administration of the precursor proteins of the invention.

A prerequisite for pharmaceutical compositions which are intended for parenteral administration is a nearly physiological pH of said compositions. Whereas mature GDF-like proteins such as GDF-5 show exceptional poor solubility under physiological conditions, the bacterially expressed precursor proteins of this invention demonstrate a pH-dependant solubility profile which allows for the direct parenteral administration to mammals. As exemplified in FIG. 8 and Example 5, they exhibit excellent solubility between pH 6 and pH 8, and especially important at or around physiological pH 7.

Whereas mature GDF-5 related proteins are insoluble at physiological pH and the use of these proteins is therefore restricted to local delivery, e.g. in combination with solid matrix materials, the excellent solubility predetermines the precursor proteins and pharmaceutical compositions of the invention for systemic delivery purposes. This allows for the efficient treatment of disorders and diseases with systemic character. The most prominent examples for such a systemic disease are osteoporosis, rheumatism and osteoarthritis. However, liquid pharmaceutical compositions such as those disclosed herein can also be efficiently used for local delivery, e.g. via injection. For example, the pharmaceutical compositions and precursor proteins of the invention are useful for the treatment of neurodegenerative disorders such as Parkinson's disease (e.g. via intracerebral infusion or intranasal delivery), for the treatment of local osteoarthritis or arthrosis (e.g. via injection into the affected tissue, organ or joint), for the regeneration of meniscus and spinal disks (e.g. via injection), for the treatment of hair loss and skin aging (e.g. via topical creams) etc. . . .

According to this novel characteristic, the precursor proteins and pharmaceutical compositions of the inventions can be administered parenterally. Such parenterally administered therapeutic compositions are typically in the form of pyrogen-free, parenterally acceptable aqueous solutions comprising the pharmaceutically effective component(s) in a pharmaceutically acceptable carrier and/or diluent. Said parenteral administration might e.g. be dermal, ocular, pulmonary, topical or intranasal administration, injection or infusion.

Of course this invention also comprises pharmaceutical compositions containing further substances like e.g. pharmacologically acceptable auxiliary and carrier substances. The formulation may include antioxidants, preservatives, colouring, flavouring and emulsifying agents, suspending agents, solvents, fillers, bulking agents, buffers such as phosphate buffered saline (PBS) or HEPES, delivery vehicles, excipients and/or pharmaceutical adjuvants. For example, a suitable carrier or vehicle may be water for injection, physiological saline solution, or a saline solution mixed with a suitable carrier protein such as serum albumin. A preferred antioxidant for the preparation of the composition of the present invention is ascorbic acid.

Cosmetic compositions known in the art, preferably hypoallergic and pH controlled are especially preferred, and include toilet waters, packs, lotions, skin milks or milky lotions. Said preparations contain, besides the active compound, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

The solvent or diluent of the pharmaceutical composition may be either aqueous or non-aqueous and may contain other pharmaceutically acceptable excipients which are capable of modifying and/or maintaining a pH, osmolarity, viscosity, clarity, scale, sterility, stability, rate of dissolution or odour of the formulation. Similarly other components may be included in the pharmaceutical composition according to the present invention in order to modify and/or maintain the rate of release of the pharmaceutically effective substance. Such modifying components are substances usually employed in the art in order to formulate dosages for parenteral administration in either unit or multi-dose form. The finally formulated pharmaceutical and/or diagnostic composition prepared according to the present invention may be stored in sterile vials in form of a solution, suspension, gel, emulsion, solid or dehydrated or lyophilized powder. These formulations may be stored either in a ready-to-use form or in a form, e.g. in case of a lyophilized powder, which requires reconstitution prior to administration. The above and further suitable pharmaceutical formulations are known in the art and are described in, for example, Gus Remington's Pharmaceutical Sciences (18th Ed., Mack Publishing Co., Eastern, Pa., 1990, 1435-1712). Such formulations may influence the physical state, stability, rate of in vivo release and rate of in vivo clearance of the pharmaceutically effective component.

The pharmaceutical composition may comprise a matrix material, i.e. in cases where regeneration of bone or cartilage is intended. It is advantageous to the precursor proteins when they are applied in and/or on a biocompatible matrix material. Matrix material as used herein means a carrier or matrix acting as a scaffold for cell recruitment, attachment, proliferation and differentiation and/or as a potential delivery and storage device for precursor proteins. In contrast to the solid matrices, carriers consist of amorphous materials having no defined surfaces and lacking a specific shape, i.e. alkylcelluloses, pluronics, gelatins, polyethylene glycols, dextrins, vegetable oils, sugars and other liquid and viscous substances.

Uses of growth factors in combination with matrix materials are extensively published and described, such as for example in WO98/21972. These matrix materials are equally suitable for precursor proteins of growth factors according to the present invention. The matrix material can be transplanted into the patient, e.g. surgically, wherein the protein or the DNA encoding the protein can be slowly released from the matrix material and then be effective over a long period of time. All types of matrix materials are useful in accordance with the present invention, as long as they are biocompatible and selected for the intended area or indication of use. The matrix material can be a natural material, a modified natural material as well as a synthetic material. All already known matrices for morphogenetic proteins are encompassed. Examples of natural materials are e.g. autologous, heterologous or xenologous bone materials, collagen, e.g. collagen type I and III, or metals like titanium. Also other components of the extracellular matrix can be used. The extracellular matrix comprises for example the various collagens, as for example types I, II, V, IX, X, XI and XIII, further proteoglycanes and glycosaminoglycanes, as for example chondroitinsulfate, biglycane, decorine and/or hyaluronic acid, or non-collagenous proteins as for example osteopontin, laminin, fibronectin, vitronectin, thrombospondin, cartilage matrix protein and dentin phosphoprotein. All mentioned natural materials may also be used in artificially modified forms. Examples of modified natural materials are demineralized bone, thermoashed bone mineral, sintered bone or chemically crosslinked hyaluronic acid (hydrogel), or metal alloys. Examples of synthetic materials are polymers like polyglycolic acid, polylactide and polylactide derivatives such as e.g. polylactic acid, poly(lactide-co-glycolide), polylactid acid-polyethylene glycol or glycolide L-lactide copolymers, further polyphosphates, polyethylene glycol, polyoxyethylene polyoxypropylene copolymers or materials containing calcium phosphates such as beta-tricalcium phosphate ($Ca_3(PO_4)2$), alpha-tricalcium phosphate and hydroxyl apatite. Further examples of other useful matrix materials belonging to one of the above mentioned groups are $Ca(OH)2$, coral, natural bone mineral, chitin, non-demineralized bone particles, ceramic bone particles, ceramic dentin, irradiated cancellous bone chips, plaster of Paris, bioactive glass, apatite-wollastonite-containing glass ceramic. Also a combination of the above mentioned carriers and/or matrices can form the matrix material as for example the combination of hydroxy apatite and collagen (e.g. Healos, previously available from Orquest, Inc., CA, USA, [now DePuy Acromed, MA, USA]), a combination of polyglycolic acid and polylactic acid or polylactid derivatives, or coral-collagen composites. For a non limiting list of useful carriers and matrices see further i.e. Kirker-Head 2000, Advanced Drug Delivery 43, 65-92.

In general, the precursor proteins or pharmaceutical compositions thereof can be applied wherever mature recombinant and wild-type GDF-5 forms have been successfully used. For example, mature GDF-5 is considered to be a very effective promoter of bone and cartilage formation as well as connective tissue formation (see for example WO 95/04819, Hötten et al. 1996, Growth Factors 13, 65-74; Storm et al. 1994, Nature 368, 639-643; Chang et al. 1994, J. Biol. Chem. 269, 28227-28234) and formation of connective tissue attachment (EP 0 831 884. In this context, GDF-5 is useful for applications concerning the joints between skeletal elements (see for example Storm & Kingsley 1996, Development 122, 3969-3979). One example for connective tissue is tendon and ligament (Wolfman et al. 1997, J. Clin. Invest. 100, 321-330; Aspenberg & Forslund 1999, Acta Orthop Scand 70, 51-54; WO 95/16035). The protein is helpful for meniscus and spinal/intervertebral disk repair (Walsh et al. 2004, Spine 29, 156-63) and spinal fusion applications (Spiro et al. 2000, Biochem Soc Trans. 28, 362-368). GDF-5 can be beneficially applied in tooth (dental and periodontal) applications (see for example WO 95/04819; WO 93/16099; Morotome et al. 1998, Biochem Biophys Res Comm 244, 85-90) such as the regeneration of dentin or periodontal ligament.

Mature GDF-5 is also useful in wound repair of any kind. It is also beneficial for promoting tissue growth in the neuronal system and survival of e.g. dopaminergic neurons. In this context, GDF-5 can be used for treating neurodegenerative disorders like e.g. Parkinson's disease and possibly also Alzheimer's disease or Huntington chorea tissues (see for example WO 97/03188; Krieglstein et al., (1995) J. Neurosci Res. 42, 724-732; Sullivan et al., (1997) Neurosci Lett 233, 73-76; Sullivan et al. (1998), Eur. J. Neurosci 10, 3681-3688). GDF-5 allows to maintain nervous function or to retain nervous function in already damaged tissues. GDF-5 is therefore considered to be a generally applicable neurotrophic factor. If e. g. nerve guide carriers are coated with GDF-5 or precursor proteins thereof, significant healing of nerve damages of the peripheral nervous systems can be anticipated.

The precursor proteins and pharmaceutical compositions of the invention can also be used for prevention or therapy of damage of periodontal or dental tissue including dental implants, neural tissue including CNS tissue and neuropathological situations, tissue of the sensory system, liver, pancreas, cardiac, blood vessel, renal, uterine and thyroid tissue, skin, mucous membranes, endothelium, epithelium, for promotion or induction of nerve growth, tissue regeneration, angiogenesis, wound healing including ulcers, burns, injuries or skin grafts, induction of proliferation of progenitor cells or bone marrow cells, for maintenance of a state of proliferation or differentiation for treatment or preservation of tissue or cells for organ or tissue transplantation; for integrity of gastrointestinal lining, for treatment of disturbances in fertility, contraception or pregnancy.

It is also useful for diseases of the eye, in particular retina, cornea and optic nerve (see for example WO 97/03188; You et al. (1999), Invest Opthalmol Vis Sci 40, 296-311), for hair growth and the treatment and diagnosis of skin related disorders (WO 02/076494; Battaglia et al. 2002, Trans. Orthop. Res. Soc. 27, 584), and for induction of angiogenesis (Yamashita et al. 1997, Exp. Cell Res. 235, 218-26).

Diseases concerning sensory organs like the eye are also to be included in the preferred indication of the pharmaceutical composition according to the invention. As preferred neuronal diseases again Parkinson's and Alzheimer's diseases can be mentioned as examples.

The following non-limiting examples together with the figures and sequence protocols are intended to further illustrate the invention.

SEQ ID NO: 1 shows the protein sequence of the human GDF-5 precursor.

SEQ ID NOs: 2 to 4 show the amino acid sequences of the cysteine domains of GDF-6, GDF-7 and GDF-5, respectively.

SEQ ID NO: 5 shows the amino acid sequence of the recombinant human GDF-5 precursor shown in FIG. 4.

FIG. 1 shows additional features of the human GDF-5 precursor protein according to SEQ ID NO: 1:

| aa 001-381 | pre-prodomain (bold letters) |
| aa 001-027 | signal peptide (bold and underlined) |
| aa 382-501 | mature protein part |
| aa 400-501 | cysteine-knot-domain (underlined) |

FIG. 2 shows a comparison of the 102 aa cysteine-knot-domains of human GDF-5 (SEQ ID NO: 4), human GDF-6 (SEQ ID NO: 2; sequence 2 from U.S. Pat. No. 5,658,882) and human GDF-7 (SEQ ID NO: 3; sequence 26 from U.S. Pat. No. 5,658,882). Amino acid residues which are identical in all three molecules are highlighted in black.

FIG. 3 shows a table with the sequence identities of cysteine-knot-domains of known BMPs and GDFs to the cysteine-knot-domain of human GDF-5.

FIG. 4 shows the amino acid sequence (SEQ ID NO: 5) of a rhGDF-5 precursor protein construct (proGDF-5) without signal peptide, but comprising an aminoterminal extension including basic stretch and thrombin cleavage site according to example 1. His-tag: bold underlined. Thrombin cleavage recognition site: underlined. rhGDF-5 pro-domain without signal peptide: boxed. Mature rhGDF-5: bold. Furin recognition site: shaded.

FIG. 5 shows a Western blot of GDF-5 precursor protein (proGDF-5, see FIG. 4) expression (see example 2) in *E. coli*. Lane 1 and 2: rhGDF-5 precursor protein expression in *E. coli* strain BL21(DE3). Lane 3 and 4: rhGDF-5 precursor protein expression in *E. coli* strain Rosetta. C: mature rhGDF-5 positive control.

FIG. 6 shows SDS PAGE analysis of rhGDF-5 precursor protein after furin digestion by SDS PAGE.

Lane 1: rhGDF-5 precursor protein after furin digestion, release of mature GDF-5 (arrow with double line). Lane 2: rhGDF-5 precursor protein (bold arrow). Lane 3: mature rhGDF-5 positive control.

Figure 9:
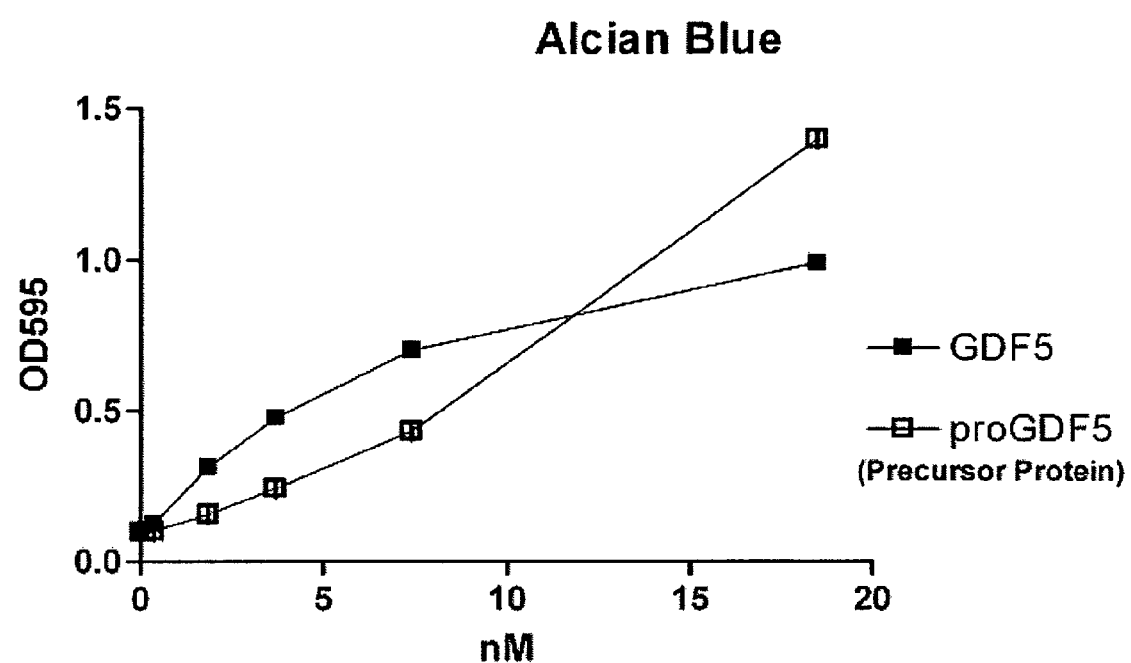

FIG. 9 shows the activation of GDF-5 precursor protein in chicken micromass cultures as described in example 6. The induction of cartilage production is indicated by the increase in Alcian blue staining. Both micromass cells incubated with mature rhGDF5 as well as with rhGDF5 precursor protein showed a massive increase of cartilage, indicating the in vivo cleavage/activation of the recombinant precursor protein outside of the trans-golgi network.

EXAMPLE 1

Creation, Expression and Purification of rhGDF-5 Precursor Proteins rhGDF-5 (recombinant human GDF-5) precursor protein without signal peptide was integrated into the protein expression vector pET15b (Novagen) using the restriction sites NdeI and BamHI. The vector codes for an N-terminal histidine tag and a thrombin cleavage site. The expression of a rhGDF-5 precursor construct (proGDF-5, see FIG. 4) was performed in the *E. coli* strains BL21(DE3) and Rosetta (Novagen). Rosetta is a BL21 derivative to enhance the expression of eukaryotic proteins that contain codons rarely used in *E. coli* the strain supply tRNAs for the codons AUA, AGG, AGA, CUA, CCC, CGG and GGA on a chloramphenicol-resistant plasmid. The protein expression was induced with IPTG, the proteins were expressed in inclusion bodies. These inclusion bodies were isolated using a homogenization buffer (25 mM Tris HCl, 10 mM EDTA, pH 7.3) and wash buffer (20 mM Tris HCl, 5 mM EDTA, pH 8.3) according to standard procedures. The inclusion bodies were solubilized in solubilization buffer (4 M GuHCl, 3 mM DTT, 0.1 M Tris HCl, pH 8.5) and the direct refolding was performed in a 1:10 dilution with refolding buffer (1 M Ariginine-HCl, 5 mM oxidized glutathione (GSSG), 1 mM reduced glutathione (GSH), 0.1 M Tris HCl, 5 mM EDTA, pH 8.0) at room temperature for 5 days. Ultrafiltration was conducted to adjust the buffer terms and to reduce the volume to an optimum load for the SEC-column. Buffer exchange was performed from 100 mM Tris HCl, 50 mM EDTA, pH 8.0 to 2 M Urea, 100 mM Tris, 150 mM NaCl, 50 mM EDTA, pH 8.0. Equipment and conditions (Ultrafiltration stiring cell; Amicon Model 8050 (50 mL), Membrane; Pall Filtron 30 kD, OM030076, Gas/Pressure; $N_2$/max. 4 bar). Further purification was carried out on a size exclusion column (GE Healthcare Amersham Biosciences, hiLoad 26/60; column material: Superdex 200 prepgrade, column volume 319 mL) flow rate 2.5 mL/min. 6 mL protein from the ultrafiltration procedure was loaded on the column. Protein was eluted in 2 M urea, 100 mM Tris HCl, 5 mM EDTA, pH 8.0. An additional purification step was carried out on reverse phase HPLC (GE Healthcare Amersham Biosciences, column HR16/10; column material Source 15RPC volume 20 mL), flow rate 3 mL/min, System: Äkta Eplorer 100. Gardient was started with 35% of Eluent B (0.1% TFA, 90% CH3N, HPLC $H_2O$) then gradient from 35% to 60%, slope 0.38%/min, then gradient 60% to 90%, slope 1.5%/min, then 90% two column volumes and finally 35%, two column volumes. The fractions containing the dimerized protein were pooled, lyophilized and stored at −80° C.

EXAMPLE 2

Analysis of rhGDF-5 Full Length Protein Expression by Western Blotting

*E. coli* strains BL21 (DE3) and Rosetta were transformed with the plasmid pET15b-rhGDF-5 full length. Protein expression was induced with IPTG. Bacterial pellets were dissolved in SDS sample buffer and separated under reducing conditions on a 16% acrylamid SDS gel. The proteins were blotted onto PVDF membrane and detected with a chemiluminescence detection kit (Applied Biosystems), using the polyclonal antibody Anti rhGDF-5 (Chicken B Pool).

Protein expression of rhGDF-5 precursor protein (GDF-5pro) could only be detected after IPTG induction. In comparison to the BL21(DE3) an increased protein expression could be achieved in the Rosetta strain. The improved protein expression in Rosetta might be due to the optimized codon usage. Protein expression was optimized with different expression vector system and different *E. coli* strains. Surprisingly, precursor protein expression was only possible when rhGDF-5 precursor had an additional N-terminal protein tag e.g. histidine tag. Protein expression of rhGDF-5 full length without N-terminal modification was not possible.

EXAMPLE 3

Cleavage of GDF-5 Precursor Protein by Furin

Figure 5:
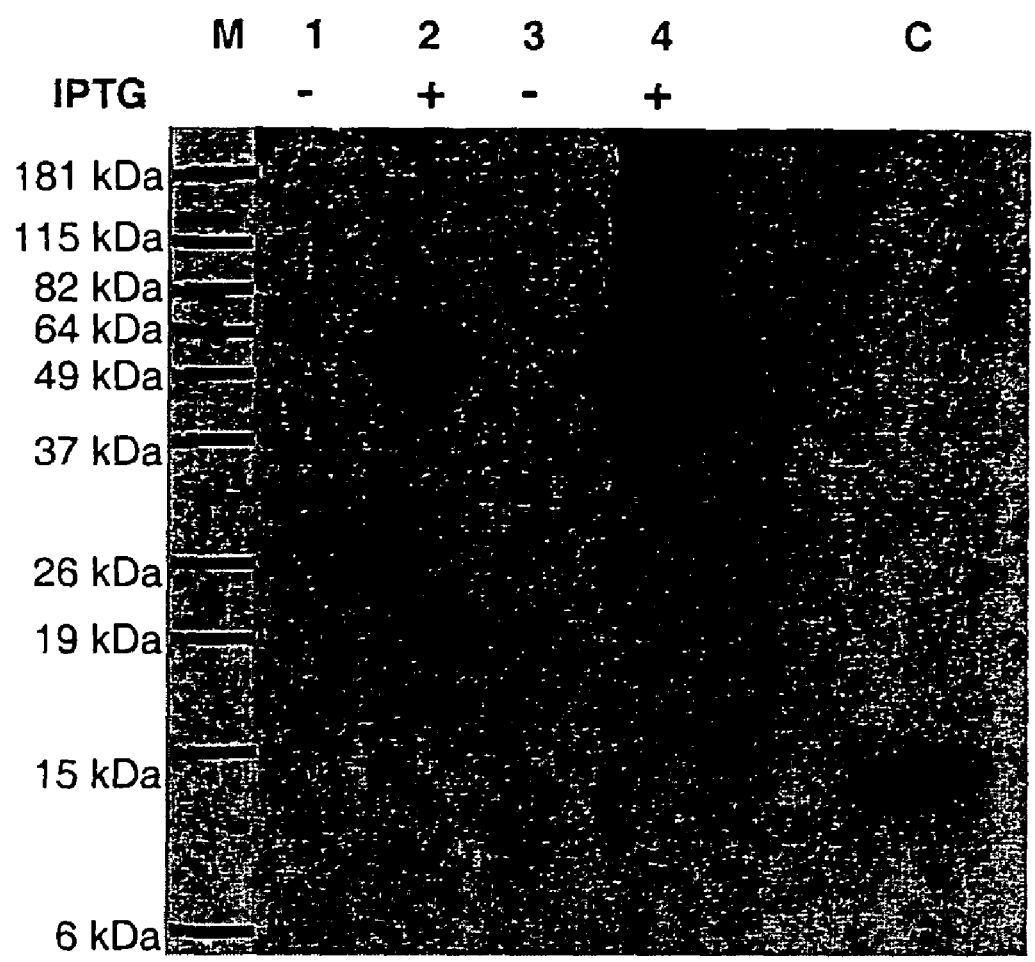
Figure 6:
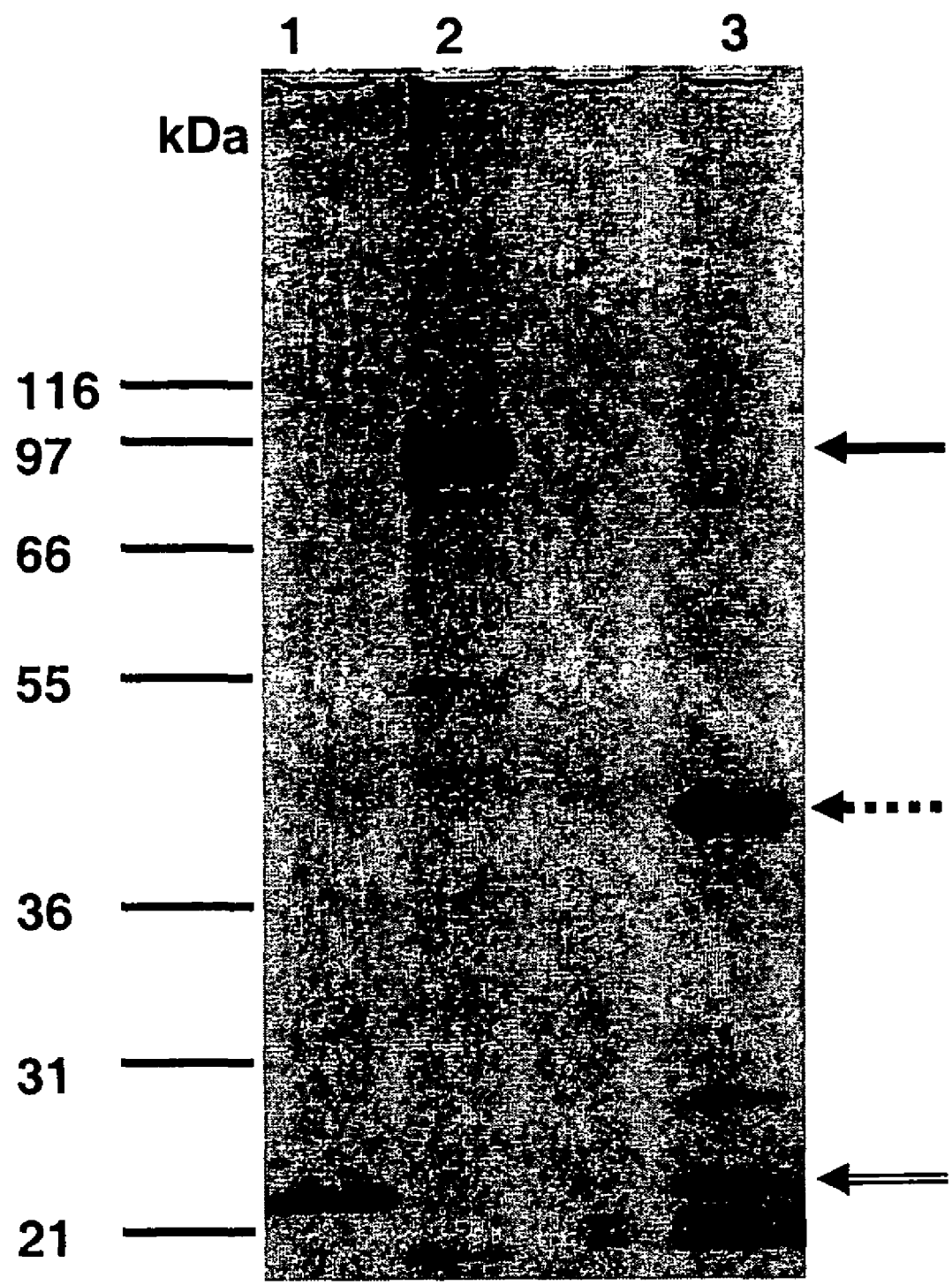

The in vitro digestion of rhGDF-5 precursor protein was performed with the specific proprotein convertase furin. Furin cleaves the amino acid recognition sequence R-K-R-R (SEQ ID NO: 6) within the rhGDF-5 full length. A typical cleavage experiment was carried out with 3 µg rhGDF-5 full length dissolved in 1× PBS supplemented with 1 mM $CaCl_2$ and incubated with 3 U Furin (New England Biolabs) at 30° C. over night. The digestion was controlled by Coomassie stained SDS gels and Western blot analysis with antibodies directed against the mature rhGDF-5. RhGDF-5 full length was digested with furin and separated under non-reducing conditions on a 10% acrylamid SDS gel (see FIG. 6). The proteins were further blotted onto PVDF membrane and detected via western blotting with a chemiluminescence detection kit (Applied Biosystems), using the mouse monoclonal antibody aMP-5.

The rhGDF-5 full length has a molecular weight of ca. 100 kDa. After digestion with furin the mature GDF-5 was released. In the western blot, aMP-5 antibody only detects correctly folded GDF-5, therefore it is demonstrated that furin generates mature rhGDF-5 from its natural precursor protein rhGDF-5 full length.

EXAMPLE 4

Figure 7:
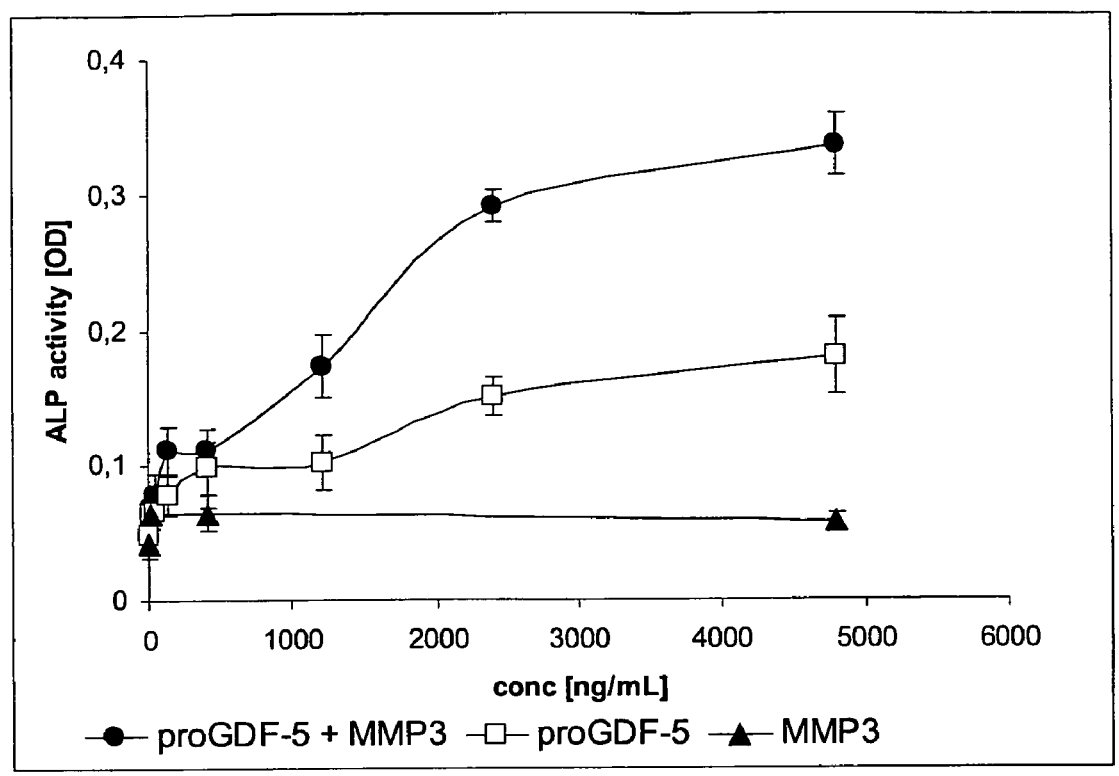
FIG. 7 shows ALP results (average values of 3 independent experiments) which are confirming proteolytical activation of rhGDF-5 precursor protein (proGDF-5) after digestion with furin, trypsin or MMP3 (control: undigested precursor protein) according to example 4. Six different protein concentrations (14.6 ng/mL, 44.5 ng/mL, 133.2 ng/mL, 400 ng/mL an 1200 ng/mL) have been used in this assay.
Figure 7:
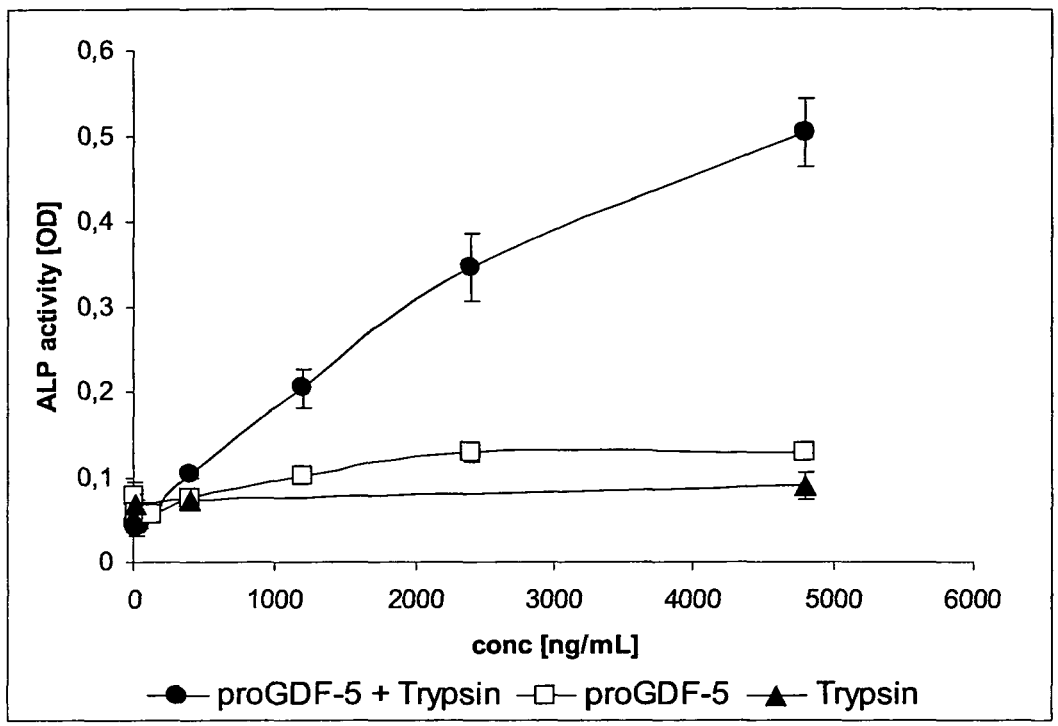
Figure 7:
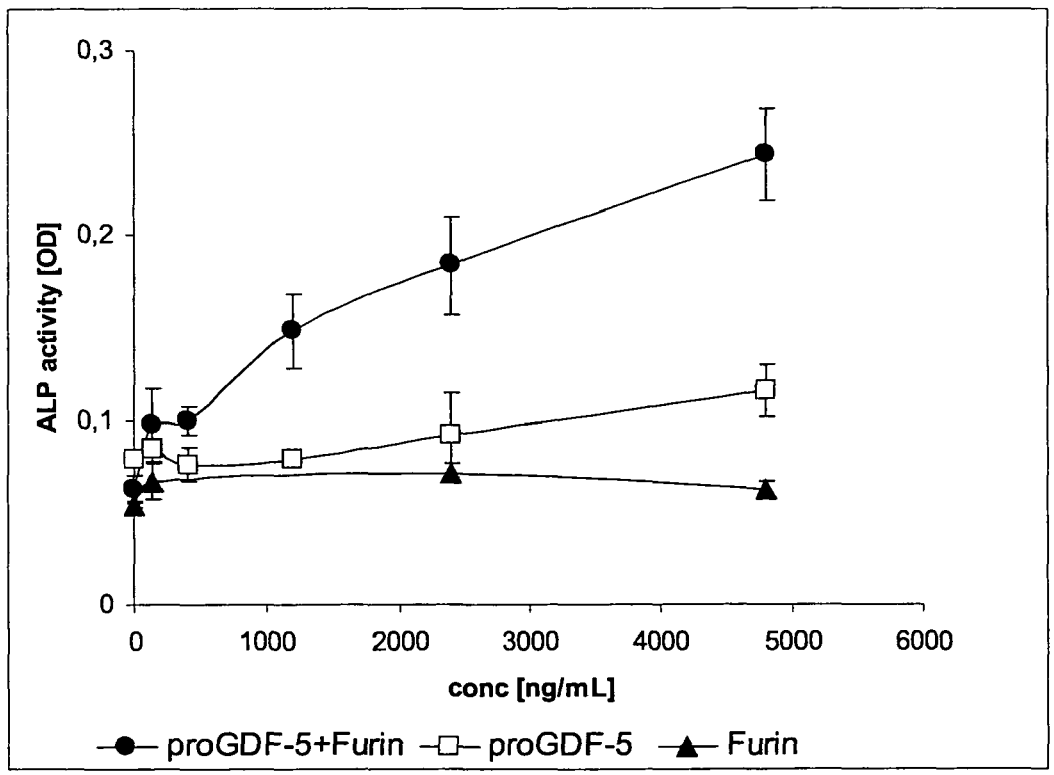
Figure 8:
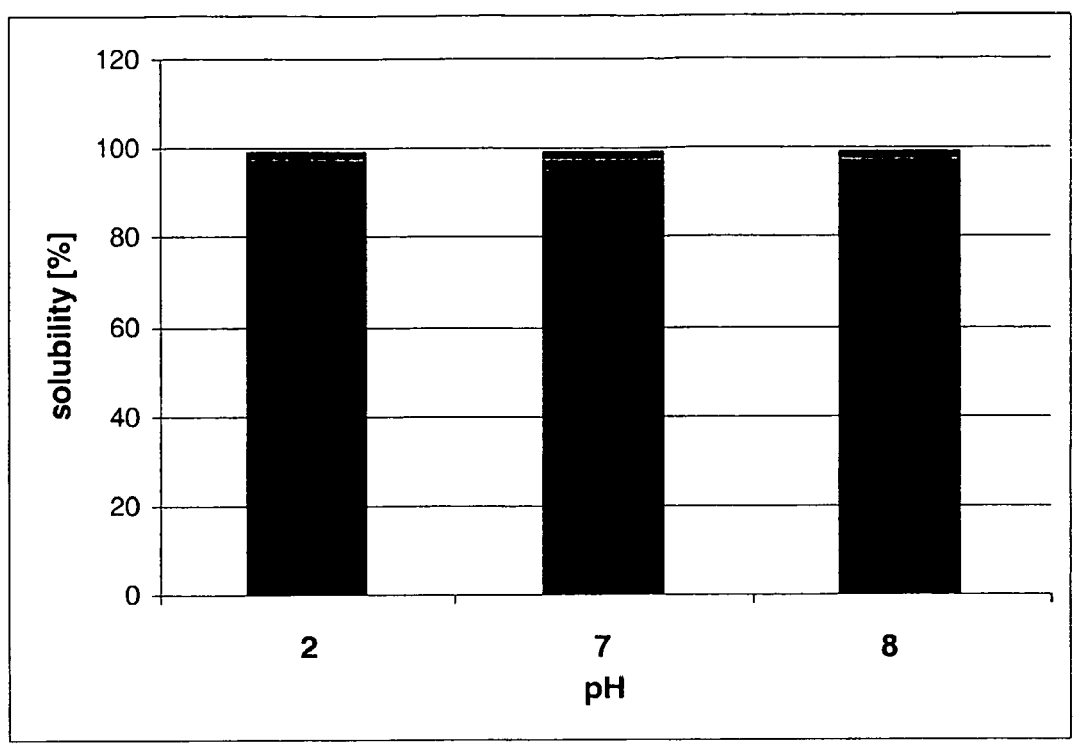
FIG. 8 shows solubility data of rhGDF-5 precursor protein according to example 5 at pH 2, pH 7 and pH8.

Measurement of the Biological Activity of rhGDF-5 Precursor Protein In Vitro by ALP Assay $5 \times 10^5$ cells of mouse stromal MCHT-1/26 cells were incubated for 3-4 days in 20 ml cell culture medium (alpha-MEM, Penicilline/Streptomycine, 2 mM L-glutamine, 10% FCS) at 37° C., 5% $CO_2$, $H_2O$-saturated. The cells were subsequently washed with PBS (phosphate buffered saline), trypsinated and resuspended in culture medium to a density of $3 \times 10^4$ cells/ml. 150 µl were transferred to each well of a 96 well culture plate and incubated for 24 h at 37° C., 5% $CO_2$, $H_2O$-saturated. After washing with medium the wells were filled with 120 µl of new culture medium. 40 µl of different dilutions of rhGDF-5 full length and rhGDF-5 for standard curve (dissolved in 10 mM HCl and diluted at least 250 fold in medium) were added, followed by another incubation step for 72 h at 37° C., 5% $CO_2$, $H_2O$-saturated. After washing with PBS, 150 µl of lysis solution (0.2% Nonidet P40, 0.2 g $MgCl_2 \times 6H_2O$, adjusted to 1000 ml with water) was added, followed by 15-18 h incubation at 37° C., 5% $CO_2$, $H_2O$-saturated. 50 µl of each well were subsequently transferred to a new 96 well plate. 50 µl of substrate solution (2.5× concentrated diethanolamine substrate buffer+148 g/l PNPP (sodium p-nitrophenyl-phosphate) was then added to each well and the plates were incubated for another 60 min at 37° C., 5% $CO_2$, $H_2O$-saturated. The ALP-reaction was stopped afterwards with 100 µl of 30 g/l NaOH and finally the optical density was measured with an automatic microplate reader at 405 nm under consideration of blank value subtraction. As an example, results (average values of 3 independent experiments) regarding rhGDF-5 precursor protein either digested with furin or undigested are shown in FIG. 7. Six different protein concentrations (14.6 ng/mL, 44.5 ng/mL, 133.2 ng/mL, 400 ng/mL an 1200 ng/mL) have been used in this assay. The undigested rhGDF-5 precursor protein protein exhibits nearly no biological activity. In contrast rhGDF-5 full length digested with furin, trypsin or MMP-3 exhibit biological activity in a dose dependent manner. The protease furin alone (as a control) has no negative influence on the ALP assay. Therefore we can conclude that rhGDF-5 precursor protein is a pro-form exhibiting no detectable biological activity in the alkaline Phosphatase assay. ALP induction of rhGDF.5 precursor protein depends on a proteolytical activation.

EXAMPLE 5

Solubility of rhGDF-5 Precursor Protein

Chromatography purified rhGDF-5 full length was eluted from a size exclusion column in 100 mM Tris HCl, 5 mM EDTA, pH 8.0 buffer. To determine the solubility protein solution (1.2 mg/mL) was adjusted with HCL to pH 2.0 and pH 7.0. Subsequently the protein solutions were centrifuged 13.000 g for 10 minutes. The supernatant was carefully removed and the pellet was solved in 10 µl SDS sample buffer. The supernatant and the pellet were separated on a 10% acrylamid SDS gel and analyzed by gel densitometry (Aida, Version 3.51)

The rhGDF-5 full length showed a solubility of 99% in a buffer comprising of 100 mM Tris HCl, 5 mM EDTA, for the pH values 2, 7, and 8. As an example for buffer with pH 7.0, 1.03 µg/100 µl protein was found in the pellet and 98 µg/100 µL was found in the supernatant. Therefore it can be concluded that rhGDF-5 full length is soluble at a physiological pH.

EXAMPLE 6

Mimicked In Vivo Activation of Protein Precursors

The micromass system is intended to mimic the initial conditions that lead to cartilage deposition in vivo. Primary cultures of undifferentiated mesenchyme cells of limb buds reproduce cartilage histogenesis, a fundamental step in the morphogenesis of the skeleton. Thus, in the micromass system, limb bud cells will form foci of differentiating chondrocytes. In order to determine a potential cleavage of the rhGDF-5 precursor protein and formation of biologically active mature protein outside the trans-Golgi network, we used chicken micromass cultures and measured cell differentiation and cartilaginous matrix production.

Micromass cultures were prepared as described previously (Lehmann et al., Proc. Natl. Acad. Sci. U.S.A. 100 (2003), 2277-12282) with minor modifications. Briefly, fertilized chicken eggs were obtained from Tierzucht Lohmann and incubated at 37.5° C. in a humidified egg incubator for about 4.5 days. Ectoderm was removed, and cells were isolated from the limb buds at stage HH23-24 by digestion with 0.1% collagenase type Ia and 0.1% trypsin. Micromass cultures were plated at a density of 2×10$^5$ cells/10-µl drop. Cells were stimulated with the proteins rhGDF-5 and rhGDF-5 precursor protein (proGDF5) respectively; increasing protein concentrations ranging from 0 to 18 nM were applied. Culture medium (DMEM-F12, 2% chicken serum, 4 mM I-glutamine, 1000 U/ml penicillin, and 100 µg/ml streptomycin) was replaced every 2 days. Alcian blue incorporation into the extracellular matrix of micromass cultures reflecting the production of proteoglycan-rich cartilaginous matrix measured at day 4 was quantified after extraction. Alcian blue staining was performed by fixing micromass cultures at day 4, then incubating with 0.1% Alcian blue, pH 1, overnight. Quantification of the staining was achieved after extensive washings with water by extraction with 6 M guanidine-HCl for 8 hours at room temperature. Dye concentration was determined spectrophotometrically at A595.

As a result, both micromass cells incubated with mature rhGDF5 as well as with rhGDF5 precursor protein showed a massive induction of cartilage production as indicated by the increase in Alcian blue staining (FIG. 9), indicating the in vivo cleavage/activation of the recombinant precursor protein outside of the trans-golgi network.

EXAMPLE 7

Removal of Aminoterminal Protein Extensions

The N-terminal extension of the GDF-5 precursor protein are removable by proteolytic processing with proteases such as thrombin, Factor Xa, enterokinase etc. Alternatively the N-terminal extension can be eliminated by autocatalytic cleavage processes induced either by pH-shift or reducing agents such as DTT or beta mercaptoethanol. For this purpose the GDF-5 precursor protein could be integrated in to the IMPACT-TWIN (Intein Mediated Purification with Affinity Chitin-binding Tag-Two Intein) system (New England Biolabs). This system utilizes the inducible self-cleavage activity of protein splicing elements termed inteins to separate the GDF-5 precursor protein from the N-terminal affinity tag. These inteins have been modified to undergo thiol-induced cleavage at their N-terminus. The use of thiol reagents such as 2-mercaptoethanesulfonic acid (MESNA) releases a reactive thioester at the C-terminus of the target protein.

7a) pH Induced Cleavage:

The rhGDF-5 precursor protein was cloned into a appropriate vector (e.g. pTWIN, containing the Ssp DnaB self-cleavable intein-tag). The resulting plasmid was transformed into an applicable *E. coli* host strain (i.e. ER2566, BL21). The cells were grown at 37° C. until an OD600 of 0.5-0.7 was reached, protein induction was induced with IPTG. For column protein purification a chitin column was equilibrated with Buffer B1 (20 mM Tris-HCl, pH 8.5, 100 mM NaCl, 1 mM EDTA). The cells were lysed in Buffer B1 and the clarified cell extract was slowly applied to the chitin column. The column was washed with Buffer B1 to remove the unbound proteins. The on-column cleavage of the intein-tag was induced by equilibrating the chitin resin in Buffer B2 (20 mM Tris-HCl, pH 7.0, 100 mM NaCl, 1 mM EDTA). To allow cleavage, the reaction was carried out overnight at room temperature. Finally the protein was eluted from the column.

7b) Thiol-Induced Cleavage:

The rhGDF-5 precursor protein was cloned into a appropriate vector (e.g. pTWIN, containing either the Mxe GyrA or Mth RIR1 intein self-cleavable intein-tag). The resulting plasmid was transformed into an applicable *E. coli* host strain (i.e. ER2566, BL21). The cells were grown at 37° C. until an OD600 of 0.5-0.7 was reached, protein induction was induced with IPTG. For column protein purification a chitin column was equilibrated with Buffer B2 (20 mM Tris-HCl, pH 7.0, 100 mM NaCl, 1 mM EDTA). The cells were lysed in Buffer B2 and the clarified cell extract was slowly applied to the chitin column. The column was washed with Buffer B2 to remove the unbound proteins. The on-column cleavage of the intein-tag was induced by equilibrating the chitin resin in Buffer B3 (20 mM Tris-HCl, pH 8.5, 100 mM NaCl, 40 mM DTT, 1 mM EDTA). To allow cleavage, the reaction was carried out overnight at room temperature. Finally the protein was eluted from the column with Buffer B3.

The invention claimed is:

1. Pharmaceutical composition comprising a mammalian precursor protein comprising a protease site necessary for proteolytic cleavage and liberation of a biologically active mature GDF-5 related protein, wherein said mammalian precursor protein is non-glycosylated, produced in prokaryotes, is biologically inactive, and is in the form of a depot formulation which is fully activated inside a mammalian body at the target site by endogenous or co-administered proteases, in combination with a pharmaceutically acceptable carrier and/or diluent.

2. The pharmaceutical composition according to claim 1, wherein the protein comprises the amino acids 28-501 of the sequence shown in SEQ ID NO: 1 representing the GDF-5 precursor without signal peptide.

3. The pharmaceutical composition according to claim 1, wherein the protein differs from SEQ ID NO: 1 in that it has an alanine residue at position 465 instead of a cysteine, wherein said protein is monomeric.

4. The pharmaceutical composition according to claim 1, further comprising an amino terminal extension of at least seven amino acids on the protein.

5. The pharmaceutical composition according to claim 4, wherein the protein comprises
   a) a recombinantly introduced protease site intended for removal of said amino terminal extension; or
   b) a recombinantly introduced site intended for pH-induced or reducing agent-induced removal of said amino terminal extension.

6. The pharmaceutical composition according to claim 1, wherein the protein comprises a recombinantly introduced continuous stretch of five or more basic amino acids wherein said amino acids are selected from the group consisting of arginine, histidine and lysine.

7. The pharmaceutical composition according to claim 1, wherein the protease site is selected from the group consisting of sites for thrombin, enterokinase, factor xa and sumo protease.

8. Pharmaceutical composition according to claim 1, wherein said composition is soluble at a pH between 6 and 8.

9. Pharmaceutical composition according to claim 8, wherein said composition is soluble at pH 7.

10. Pharmaceutical composition according to claim 1, said composition further comprising a protease formulation necessary for proteolytic release of the mature protein.

11. Pharmaceutical composition according to claim 10, said protease formulation comprising one or more proteases selected from the group consisting of matrix proteases and subtilisin like proprotein convertases.

12. Pharmaceutical composition according to claim 10, said protease formulation providing retarded release of said proteases.

13. Pharmaceutical composition according to claim 10, wherein said protease formulation comprises one or more proteases which are selected from the group consisting of furin, SPC-4 and SPC-6.

14. Pharmaceutical composition according to claim 10, wherein said protease formulation comprises a combination of either SPC-1 (furin) and SPC-6, SPC-1 (furin) and SPC-4, or SPC-1 (furin) and SPC-7.

15. Pharmaceutical composition according to claim 1 which is formulated for parenteral administration.

16. Pharmaceutical composition according to claim 15, wherein said parenteral administration is an injection or intracerebral infusion.

17. Pharmaceutical composition according to claim 15, wherein said parenteral administration is dermal, ocular, pulmonary, topical or intranasal administration.

18. An isolated DNA molecule encoding a mammalian precursor protein comprising a protease site necessary for proteolytic cleavage and liberation of a biologically active mature GDF-5 related protein, wherein the triplets AUA (Ile), AGG (Arg), AGA (Arg), CGG (Arg), CGA (Arg), CUA (Leu), CCC (Pro) and GGA (Gly) within the first 30 codons have been replaced by alternative triplets of the genetic code encoding identical amino acids, wherein said mammalian precursor protein is non-glycosylated, produced in prokaryotes, and biologically inactive.

19. An isolated DNA molecule encoding, a mammalian precursor protein comprising a protease site necessary for proteolytic cleavage and liberation of a biologically active mature GDF-5 related protein, wherein stretches of at least two triplets selected from the group consisting of AUA (Ile), AGG (Arg), AGA (Arg), CGG (Arg), CGA (Arg), CUA (Leu), CCC (Pro) and GGA (Gly) within the first 30 codons have been replaced by alternative triplets of the genetic code encoding identical amino acids, wherein said mammalian precursor protein is non-glycosylated, can be produced in prokaryotes, and is biologically inactive.

20. A process of manufacturing a mammalian precursor protein comprising a protease site necessary for proteolytic cleavage and liberation of a biologically active mature GDF-5 related protein in prokaryotic host cells, comprising transforming a prokaryotic host cell with a plasmid containing a DNA molecule encoding the precursor protein, wherein the triplets AUA (Ile), AGG (Arg), AGA (Arg), CGG (Arg), CGA (Arg), CUA (Leu), CCC (Pro) and GGA (Gly) within the first 30 codons have been replaced by alternative triplets of the genetic code encoding identical amino acids.

21. The process according to claim 20, further comprising solubilization of inclusion bodies in a solution comprising 3 mM DTT or less.

22. The process according to claim 21, further comprising a direct refolding procedure which comprises a step of diluting the inclusion body solution 10 fold or less.

23. The process according to claim 20, characterized in that said process comprises a step of transforming a prokaryotic host cell with a plasmid containing a DNA molecule encoding said precursor protein, characterized in that stretches of at least two triplets selected from the group consisting of AUA (He), AGG, AGA, CGG, CGA (Arg), CUA (Leu), CCC (Pro) and GGA (Gly) within the first 30 codons have been replaced by alternative triplets of the genetic code encoding identical amino acids.

* * * * *

SEQUENCE LISTING

```
<160> NUMBER OF SEQ ID NOS: 14

<210> SEQ ID NO 1
<211> LENGTH: 501
<212> TYPE: PRT
<213> ORGANISM: Homo sapiens
<220> FEATURE:
<221> NAME/KEY: MISC_FEATURE
<222> LOCATION: (1)..(501)
<223> OTHER INFORMATION: human GDF-5 precursor

<400> SEQUENCE: 1

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
```

-continued

```
              65                  70                  75                  80
Gly Gln Thr Gly Gly Leu Thr Gln Pro Lys Lys Asp Glu Pro Lys Lys
                        85                  90                  95
Leu Pro Pro Arg Pro Gly Gly Pro Glu Pro Lys Pro Gly His Pro Pro
                   100                 105                 110
Gln Thr Arg Gln Ala Thr Ala Arg Thr Val Thr Pro Lys Gly Gln Leu
                  115                 120                 125
Pro Gly Gly Lys Ala Pro Lys Ala Gly Ser Val Pro Ser Ser Phe
                130                 135                 140
Leu Leu Lys Lys Ala Arg Glu Pro Gly Pro Pro Arg Glu Pro Lys Glu
145                 150                 155                 160
Pro Phe Arg Pro Pro Ile Thr Pro His Glu Tyr Met Leu Ser Leu
                        165                 170                 175
Tyr Arg Thr Leu Ser Asp Ala Asp Arg Lys Gly Gly Asn Ser Ser Val
                    180                 185                 190
Lys Leu Glu Ala Gly Leu Ala Asn Thr Ile Thr Ser Phe Ile Asp Lys
                195                 200                 205
Gly Gln Asp Asp Arg Gly Pro Val Val Arg Lys Gln Arg Tyr Val Phe
                210                 215                 220
Asp Ile Ser Ala Leu Glu Lys Asp Gly Leu Leu Gly Ala Glu Leu Arg
225                 230                 235                 240
Ile Leu Arg Lys Lys Pro Ser Asp Thr Ala Lys Pro Ala Ala Pro Gly
                        245                 250                 255
Gly Gly Arg Ala Ala Gln Leu Lys Leu Ser Ser Cys Pro Ser Gly Arg
                260                 265                 270
Gln Pro Ala Ser Leu Leu Asp Val Arg Ser Val Pro Gly Leu Asp Gly
                275                 280                 285
Ser Gly Trp Glu Val Phe Asp Ile Trp Lys Leu Phe Arg Asn Phe Lys
                290                 295                 300
Asn Ser Ala Gln Leu Cys Leu Glu Leu Glu Ala Trp Glu Arg Gly Arg
305                 310                 315                 320
Ala Val Asp Leu Arg Gly Leu Gly Phe Asp Arg Ala Ala Arg Gln Val
                        325                 330                 335
His Glu Lys Ala Leu Phe Leu Val Phe Gly Arg Thr Lys Lys Arg Asp
                340                 345                 350
Leu Phe Phe Asn Glu Ile Lys Ala Arg Ser Gly Gln Asp Asp Lys Thr
                355                 360                 365
Val Tyr Glu Tyr Leu Phe Ser Gln Arg Arg Lys Arg Arg Ala Pro Leu
                370                 375                 380
Ala Thr Arg Gln Gly Lys Arg Pro Ser Lys Asn Leu Lys Ala Arg Cys
385                 390                 395                 400
Ser Arg Lys Ala Leu His Val Asn Phe Lys Asp Met Gly Trp Asp Asp
                        405                 410                 415
Trp Ile Ile Ala Pro Leu Glu Tyr Glu Ala Phe His Cys Glu Gly Leu
                420                 425                 430
Cys Glu Phe Pro Leu Arg Ser His Leu Glu Pro Thr Asn His Ala Val
                435                 440                 445
Ile Gln Thr Leu Met Asn Ser Met Asp Pro Glu Ser Thr Pro Pro Thr
                450                 455                 460
Cys Cys Val Pro Thr Arg Leu Ser Pro Ile Ser Ile Leu Phe Ile Asp
465                 470                 475                 480
Ser Ala Asn Asn Val Val Tyr Lys Gln Tyr Glu Asp Met Val Val Glu
                        485                 490                 495
```

```
Ser Cys Gly Cys Arg
            500

<210> SEQ ID NO 2
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: cysteine-knot-domain of human GDF-6

<400> SEQUENCE: 2

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
                20                  25                  30

Val Cys Asp Phe Pro Leu Arg Ser His Leu Glu Pro Thr Asn His Ala
            35                  40                  45

Ile Ile Gln Thr Leu Met Asn Ser Met Asp Pro Gly Ser Thr Pro Pro
        50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
            100

<210> SEQ ID NO 3
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: cysteine-knot-domain of human GDF-7

<400> SEQUENCE: 3

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
                20                  25                  30

Leu Cys Asp Phe Pro Leu Arg Ser His Leu Glu Pro Thr Asn His Ala
            35                  40                  45

Ile Ile Gln Thr Leu Leu Asn Ser Met Ala Pro Asp Ala Ala Pro Ala
        50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100

<210> SEQ ID NO 4
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: cysteine-knot-domain of human GDF-5

<400> SEQUENCE: 4
```

```
Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 5
<211> LENGTH: 495
<212> TYPE: PRT
<213> ORGANISM: Homo sapiens
<220> FEATURE:
<221> NAME/KEY: MISC_FEATURE
<222> LOCATION: (1)..(495)
<223> OTHER INFORMATION: recombinant human GDF-5 precursor

<400> SEQUENCE: 5

Met Gly Ser Ser His His His His His His Ser Ser Gly Leu Val Pro
1               5                   10                  15

Arg Gly Ser His Met Ala Pro Asp Leu Gly Gln Arg Pro Gln Gly Thr
            20                  25                  30

Arg Pro Gly Leu Ala Lys Ala Glu Ala Lys Glu Arg Pro Pro Leu Ala
        35                  40                  45

Arg Asn Val Phe Arg Pro Gly Gly His Ser Tyr Gly Gly Gly Ala Thr
50                  55                  60

Asn Ala Asn Ala Arg Ala Lys Gly Gly Thr Gly Gln Thr Gly Gly Leu
65                  70                  75                  80

Thr Gln Pro Lys Lys Asp Glu Pro Lys Lys Leu Pro Pro Arg Pro Gly
                85                  90                  95

Gly Pro Glu Pro Lys Pro Gly His Pro Pro Gln Thr Arg Gln Ala Thr
            100                 105                 110

Ala Arg Thr Val Thr Pro Lys Gly Gln Leu Pro Gly Gly Lys Ala Pro
        115                 120                 125

Pro Lys Ala Gly Ser Val Pro Ser Ser Phe Leu Leu Lys Lys Ala Arg
130                 135                 140

Glu Pro Gly Pro Pro Arg Glu Pro Lys Glu Pro Phe Arg Pro Pro Pro
145                 150                 155                 160

Ile Thr Pro His Glu Tyr Met Leu Ser Leu Tyr Arg Thr Leu Ser Asp
                165                 170                 175

Ala Asp Arg Lys Gly Gly Asn Ser Ser Val Lys Leu Glu Ala Gly Leu
            180                 185                 190

Ala Asn Thr Ile Thr Ser Phe Ile Asp Lys Gly Gln Asp Asp Arg Gly
        195                 200                 205

Pro Val Val Arg Lys Gln Arg Tyr Val Phe Asp Ile Ser Ala Leu Glu
210                 215                 220

Lys Asp Gly Leu Leu Gly Ala Glu Leu Arg Ile Leu Arg Lys Lys Pro
225                 230                 235                 240

Ser Asp Thr Ala Lys Pro Ala Ala Pro Gly Gly Gly Arg Ala Ala Gln
```

```
                        245                 250                 255
Leu Lys Leu Ser Ser Cys Pro Ser Gly Arg Gln Pro Ala Ser Leu Leu
                260                 265                 270

Asp Val Arg Ser Val Pro Gly Leu Asp Gly Ser Gly Trp Glu Val Phe
            275                 280                 285

Asp Ile Trp Lys Leu Phe Arg Asn Phe Lys Asn Ser Ala Gln Leu Cys
        290                 295                 300

Leu Glu Leu Glu Ala Trp Glu Arg Gly Arg Ala Val Asp Leu Arg Gly
305                 310                 315                 320

Leu Gly Phe Asp Arg Ala Ala Arg Gln Val His Glu Lys Ala Leu Phe
                325                 330                 335

Leu Val Phe Gly Arg Thr Lys Lys Arg Asp Leu Phe Phe Asn Glu Ile
                340                 345                 350

Lys Ala Arg Ser Gly Gln Asp Asp Lys Thr Val Tyr Glu Tyr Leu Phe
            355                 360                 365

Ser Gln Arg Arg Lys Arg Arg Ala Pro Leu Ala Thr Arg Gln Gly Lys
        370                 375                 380

Arg Pro Ser Lys Asn Leu Lys Ala Arg Cys Ser Arg Lys Ala Leu His
385                 390                 395                 400

Val Asn Phe Lys Asp Met Gly Trp Asp Asp Trp Ile Ile Ala Pro Leu
                405                 410                 415

Glu Tyr Glu Ala Phe His Cys Glu Gly Leu Cys Glu Phe Pro Leu Arg
                420                 425                 430

Ser His Leu Glu Pro Thr Asn His Ala Val Ile Gln Thr Leu Met Asn
            435                 440                 445

Ser Met Asp Pro Glu Ser Thr Pro Pro Thr Cys Cys Val Pro Thr Arg
450                 455                 460

Leu Ser Pro Ile Ser Ile Leu Phe Ile Asp Ser Ala Asn Asn Val Val
465                 470                 475                 480

Tyr Lys Gln Tyr Glu Asp Met Val Val Glu Ser Cys Gly Cys Arg
                485                 490                 495

<210> SEQ ID NO 6
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: recognition sequence for Furin cleavage
      within rhGDF-5

<400> SEQUENCE: 6

Arg Lys Arg Arg
1

<210> SEQ ID NO 7
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: N-terminus sequence of fusion protein

<400> SEQUENCE: 7

His His His His His
1               5

<210> SEQ ID NO 8
```

```
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: N-terminus of fusion protein

<400> SEQUENCE: 8

Leu Leu Leu Leu Leu
1               5

<210> SEQ ID NO 9
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: N-terminus of fusion protein

<400> SEQUENCE: 9

Arg Arg Arg Arg Arg
1               5

<210> SEQ ID NO 10
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: N-terminus of fusion protein

<400> SEQUENCE: 10

His Leu His Leu His
1               5

<210> SEQ ID NO 11
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: N-terminus of fusion protein

<400> SEQUENCE: 11

Arg His Arg His Arg
1               5

<210> SEQ ID NO 12
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Proteolytic cleavage site of recombinant
      precursor proteins of the invention at which mature peptide
      divides from the amino-terminal prodomain
<220> FEATURE:
<221> NAME/KEY: MISC_FEATURE
<222> LOCATION: (2)..(2)
<223> OTHER INFORMATION: This residue may be any amino acid.
<220> FEATURE:
<221> NAME/KEY: MISC_FEATURE
<222> LOCATION: (3)..(3)
<223> OTHER INFORMATION: This residue may be either K or R.

<400> SEQUENCE: 12
```

```
Arg Xaa Lys Arg
1

<210> SEQ ID NO 13
<211> LENGTH: 4
<212> TYPE: PRT
<213> ORGANISM: Homo sapiens
<220> FEATURE:
<221> NAME/KEY: misc_feature
<222> LOCATION: (1)..(4)
<223> OTHER INFORMATION: Proteolytic cleavage site of human GDF-5 at
      which mature peptide divides from the amino-terminal prodomain

<400> SEQUENCE: 13

Arg Arg Lys Arg
1

<210> SEQ ID NO 14
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Proteolytic cleavage site of GDF-6 and GDF-7
      at which mature peptide divides from the amino-terminal prodomain

<400> SEQUENCE: 14

Arg Arg Arg Arg
1
```